(12) United States Patent
Walt et al.

(10) Patent No.: US 7,480,433 B2
(45) Date of Patent: Jan. 20, 2009

(54) ELECTRO-OPTICAL STIMULATION/MEASUREMENT

(75) Inventors: David R. Walt, Lexington, MA (US); Sabine Szunerits, Grenoble (FR)

(73) Assignee: Tufts University, Medford, MA (US)

( * ) Notice: Subject to any disclaimer, the term of this patent is extended or adjusted under 35 U.S.C. 154(b) by 6 days.

(21) Appl. No.: 10/503,995

(22) PCT Filed: Feb. 14, 2003

(86) PCT No.: PCT/US03/04700
§ 371 (c)(1),
(2), (4) Date: Jul. 8, 2005

(87) PCT Pub. No.: WO03/071223
PCT Pub. Date: Aug. 28, 2003

(65) Prior Publication Data
US 2006/0013543 A1 Jan. 19, 2006

(51) Int. Cl.
*G02B 6/06* (2006.01)
(52) U.S. Cl. ............... 385/116; 385/115; 385/117; 385/118; 385/119
(58) Field of Classification Search .......... 385/115–121
See application file for complete search history.

(56) References Cited

U.S. PATENT DOCUMENTS

| | | | |
|---|---|---|---|
| 5,784,156 A * | 7/1998 | Nicholson | 356/141.5 |
| 6,032,062 A | 2/2000 | Nisch | 600/372 |
| 6,072,619 A | 6/2000 | Kiryuschev et al. | 359/245 |
| 6,821,009 B2 * | 11/2004 | Ohkubo | 362/554 |
| 6,859,594 B2 * | 2/2005 | Cheng et al. | 385/120 |
| 2002/0031315 A1 * | 3/2002 | Cheng et al. | 385/120 |
| 2002/0172478 A1 * | 11/2002 | Sahlin | 385/115 |
| 2005/0058414 A1 * | 3/2005 | Kochergin | 385/120 |

OTHER PUBLICATIONS

International Search Report for Application No. PCT/US03/04700 dated Sep. 23, 2003.
Kobayashi, Y., Martin, C.R., "Highly Sensitive Methods For Electroanalytical Chemistry Based On Nanotubule Membranes", Anal. Chem., 1999, vol. 71, pp. 3665-3672.
Bronk, K.S., Michael, K.L., Pantono, P., Walt, D.R., "Combined Imaging And Chemical Sensing Using A Single Optical Imaging Fiber", Anal. Chem., 1995, vol. 67, pp. 2750-2757.

(Continued)

*Primary Examiner*—Frank G Font
*Assistant Examiner*—Eric Wong
(74) *Attorney, Agent, or Firm*—Mintz, Levin, Cohn, Ferris, Glovsky and Popeo PC (57) ABSTRACT

An electro-optical system includes an array including a plurality of optical fibers and a plurality of electrodes, and an insulator. The optical fibers are configured to transmit light, the optical fibers being mechanically coupled at distal ends in a distal arrangement and mechanically coupled at proximal ends in a proximal arrangement. The plurality of electrodes are substantially coaxially disposed with at least portions of corresponding optical fibers, the electrodes being electrically conductive, with the electrodes and optical fibers being disposed in pairs, thereby being pair components, with one of the pair components of each pair being disposed about a radial periphery of the other pair component. The insulator is disposed between the plurality of electrodes and configured to inhibit transfer of electrical energy between the plurality of electrodes.

39 Claims, 9 Drawing Sheets

OTHER PUBLICATIONS

Wallingford, R. A., Correspondence, "Capillary Zone Electrophoresis with Electrochemical Detector in 12.7mm Diameter Columns", Anal. Chem., 1988, vol. 60, pp. 1972-1975.

Szabo, A., "Theory of the Current at Microelectrodes: Application to Ring Electrodes", J. Phys. Chem., 1987, vol. 91, pp. 3108-3111.

Fleischmann, M., Pons, S., "The Behavior Of Microdisk And Microring Electrodes", J. Electroanal. Chem., 1987, vol. 222, pp. 107-115.

Gerardi, R.D., Barnett, N.W., Lewis, S.W., "Analytical Applications of tris(2,2'-bipyridyl)ruthenium(III) As A Chemiluminescent Reagent", Analytica Chimica Acta, 1999, vol. 378, pp. 1-41.

Gao, L., Seliskar, C.J., Heineman, W.R., "Spectroelectrochemical Sensing Based On A Multimode Selectivity Simultaneously Achievable In A Single Device. 8. Selectivity at Poly(vinyl alcohol)-Polyelectrolyte Blend Modified Optically Transparent Electrodes", Electroanalysis, 2001, vol. 13, No. 8-9, pp. 613-620.

* cited by examiner

ELECTRO-OPTICAL STIMULATION/MEASUREMENT

STATEMENT AS TO FEDERALLY-SPONSORED RESEARCH

This invention was made at least in part with Government support under Grant No. GM48142, awarded by National Institutes of Health. The Government has certain rights in this invention.

FIELD OF THE INVENTION

The invention relates to dual sensor/actuator systems and more particularly to combination optical and electrical sensor/actuator arrays.

BACKGROUND OF THE INVENTION

There is a virtually endless list of applications for devices that can provide stimuli to and/or receive output from and/or detect states of any number of systems, including living beings, machines, chemicals, etc. For example, conductors can deliver energy to systems, such as delivering electricity to a muscle to stimulate contraction of the muscle. Also, conductors can be used to sense electric impulses produced internally to a body to determine when or whether the body has instructed the muscle to contract. Optical fibers can deliver light to systems, e.g., to cause a reaction that can be detected by optical fibers, or other means such as electrical conductors. Beside electrochemical devices, optical fibers and optical fiber bundles allowing simultaneous sensing and imaging have been used increasingly for a variety of different applications.

As technology advances, there is a push toward smaller, faster, more quickly responsive actuators and sensors. Microelectrodes provide small voltage-drop devices for transferring energy, be it for providing stimuli or measuring electrical output. Microelectrodes are gaining increased importance in electrochemical analysis and sensor technology as their small size leads to small faradaic currents, reduced iR drop and steady-state diffusion currents.

SUMMARY OF THE INVENTION

In general, in an aspect, the invention provides an electro-optical system including an array including a plurality of optical fibers, a plurality of electrodes, and an insulator. The optical fibers are configured to transmit light, the optical fibers being mechanically coupled at distal ends in a distal arrangement and mechanically coupled at proximal ends in a proximal arrangement. The plurality of electrodes are substantially coaxially disposed with at least portions of corresponding optical fibers, the electrodes being electrically conductive, with the electrodes and optical fibers being disposed in pairs, thereby being pair components, with one of the pair components of each pair being disposed about a radial periphery of the other pair component. The insulator is disposed between the plurality of electrodes and configured to inhibit transfer of electrical energy between the plurality of electrodes.

Implementations of the invention may include one or more of the following features. The system further includes an electrical apparatus coupled to at least some of the plurality of electrodes and configured to at least one of transmit electrical energy to, and receive electrical energy from, the at least some of the plurality of electrodes, and an optical apparatus configured and disposed to receive light from the proximal ends of the optical fibers. The electrical device is coupled to less than all the plurality of electrodes. The electrical device is coupled to a percentage of the electrodes such that diffusional overlap at distal ends of the electrodes will be substantially negligible. The electrical device is coupled to approximately 20-30% of the electrodes. The electrode of each pair is disposed about the radial periphery of the fiber of each pair. An edge-to-edge spacing between any two electrodes coupled to the electrical apparatus is greater than about 10 times a typical diameter of one the plurality of electrodes. The optical fiber of each pair is disposed about the radial periphery of the electrode of each pair. A center-to-center spacing between any two electrodes disposed coaxially with the at least some of the plurality of optical fibers is greater than about 10 times a typical diameter of one the plurality of electrodes. The distal ends of the optical fibers correlate to the proximal ends of the optical fibers in a known manner. The distal arrangement and the proximal arrangement are substantially similar. The electrical apparatus is configured to at least one of transfer electrical energy to, and receive electrical energy from, the at least some of the plurality of electrodes as a group. The electrical apparatus is configured to at least one of transfer electrical energy to, and receive electrical energy from, the at least some of the plurality of electrodes individually. The electrodes comprise electrically-conductive material coating an outer surface of the optical fibers.

In general, in another aspect, the invention provides a method of stimulating and sensing an object, the method including providing energy in a first form to the object through at least one of a plurality of first energy transmitters disposed in a first array at least at distal ends of the first energy transmitters, the first form of energy being one of electrical and optical, and sensing energy in a second form, produced by the object, through at least one of a plurality of second energy transmitters disposed in a second array at least at distal ends of the second energy transmitters, the first and second energy transmitters being mechanically coupled together and coaxially disposed at least at their distal ends, the second form of energy being one of electrical and optical, the second form of energy being different than the first form of energy.

Implementations of the invention may include one or more of the following features. The first form of energy is electrical and the first energy transmitters are microelectrodes, and wherein the providing energy includes providing energy to all of the plurality of first energy transmitters. The first form of energy is electrical and the first energy transmitters are microelectrodes, and wherein the providing energy includes selectively providing energy to a portion of the plurality of first energy transmitters. The method of claim 16 wherein the providing energy includes providing energy to the portion of the plurality of first energy transmitters such that diffusional overlap of the energy at distal ends of the portion of the plurality of first energy transmitters is substantially negligible. The first form of energy is electrical and the first energy transmitters are microelectrodes, and wherein the providing energy includes providing different amounts of energy to different ones of the plurality of first energy transmitters. Either the first or the second energy transmitters are electrodes, the method further comprising providing electrical energy through the electrodes to kill living tissue in the object in a vicinity of distal ends of the electrodes. The method further includes processing the second energy to determine an image of at least a portion of the object. The method further includes providing energy in the second form to the object through at least one of the second energy transmitters. The providing energy in the first form and the providing energy in the second form occurs concurrently. The second energy transmitters are optical fibers, and the sensing includes sensing optical energy transmitted by at least two of the optical fibers. The first energy transmitters are optical fibers and the providing includes transmitting optical energy through less than all of the optical fibers.

In general, in another aspect, the invention provides an electro-optical actuator/sensor system including optical means for delivering light to an optical-fiber array, electrical means for delivering electricity through an electrical array of microelectrodes, the electrical means comprising electrically-conductive cladding of the optical fibers in the optical-fiber array, an electrical apparatus coupled to the electrical means and configured to transfer electrical energy between the electrical apparatus and selected ones of the microelectrodes, and an optical apparatus configured and disposed to transfer light between the apparatus and the optical-fiber array.

Implementations of the invention may include one or more of the following features. Distal and proximal ends of the optical fibers and electrodes are coherently related. The electrical apparatus is coupled to transfer electrical energy to about 20-30% of the electrodes. Distal ends of the electrodes are disposed proximate to distal ends of the optical fibers and are separated from each other such that diffusional overlap associated with the electrodes is substantially negligible.

Various percentages or portions of energy transmitters in arrays can be stimulated to reduce or eliminate effects of diffusional overlap in a subject receiving energy from the arrays. As diffusional overlap is dependent upon size of the element radiating energy, and time of stimulation/activation, the number of elements activated may be adjusted to reduce or eliminate diffusional overlap. All elements can be activated if the separation between elements combined with the size of elements, amount of time of stimulation, size of species, viscosity of solution, applied current amount, and any other influencing factors, results in little or no diffusional overlap. Preferably, less than all elements are stimulated to help ensure negligible overlap. Any percentage under 100% can be used if, when combined with diffusional-overlap-influencing factors (e.g., element size, current, solution viscosity, species size, and time of stimulation), the overlap can be neglected. Arrays with approximately 50% and between 20-30% of the elements activated proved successful in acceptably controlling diffusional overlap.

The invention also provides a method of specifically stimulating a target cell in a population of non-target cells by detecting an optical signal (e.g., a signal elaborated after binding of the cell to a detectably labeled antibody or other cell-specific ligand) to identify the target cell and deliver an electrical current to the cell. The electrical current preferably is not delivered to a non-target cell, which may be present in the population of cells (e.g., adjacent to the target cell). The electrical current stimulates the target cell to transduce an intracellular or extracellular signal, e.g, the target cell is stimulated to produce a neurotransmitter or cytokine. The target cell may also be stimulated to proliferate. Alternatively, the target cell is identified electrically and stimulated by focusing an optical beam on the target cell.

A method of specifically destroying or inhibiting the growth of a target cell in population of non-target cells is carried out by detecting an optical signal (as described above) to identify the target cell and delivering an electrical current to the cell thereby inhibiting proliferation of the target cell or destroying the target cell. For example, the target cell is a cancer cell and non-target cells are healthy (non-tumor) cells present in a bodily tissue. The electrical current is preferably not delivered to a non-target cell, i.e., the target cell is destroyed while sparing non-target (e.g, healthy) cells, which are present in the heterogeneous cell population or bodily tissue. The specificity of the cell targeting method reduces undesirable side effects (e.g., death of healthy cells) often associated with known cancer therapies.

Various aspects of the invention may provide one or more of the following advantages. Higher currents than using a single ring-shaped microelectrode may be achieved without losing benefits gained by miniaturization. Rapid response time, steady state diffusion layer, and small iR drops may be achieved for electric transmission while providing high currents. Uses and advantages of microelectrodes can be combined with imaging properties of optical fiber bundles. Diffusional overlap of microelectrodes may be reduced/limited. Optical and electronic, including electrochemical, stimulation and measuring may be performed with a single apparatus. Microelectrode sensor/actuator signal-to-noise ratio may be improved.

These and other advantages of the invention, along with the invention itself, will be more fully understood after a review of the following figures, detailed description, and claims.

DETAILED DESCRIPTION OF PREFERRED EMBODIMENTS

The invention provides novel optoelectric and optoelectrochemical micro-ring arrays and techniques for fabricating such arrays. The arrays include multiple optical fibers coated with electrically conducting material, to serve as microelectrodes disposed about the optical fibers. An exemplary array was fabricated and tested. The array was fabricated by coating individual optical fibers of 25 µm diameter with a 1 µm layer of gold nanoparticles via electroless gold deposition. A self-assembled thiol monolayer (SAM layer) around the individual gold-coated imaging fibers helped prevent electrical contact with neighboring ring-electrodes. To achieve better mechanical stability and to make the device more practical, the electrode/fiber bundle comprising approximately 600 individual gold-coated optical fibers was dipped into epoxy. By polishing the ends of such a device, a ring microelectrode array comprising 600 individual and insulated ring electrodes was formed. To limit diffusional overlap of current, only 20-30% of the micro-ring fiber/electrodes were wired. The inner diameter of the ring electrode is fixed by the diameter of the individual optical fibers (25 µm), while the outer radius is determined by the thickness of the deposited gold. The array was characterized using ferrocyanide in aqueous solution as a model electroactive species to demonstrate that this microelectrode array format exhibits steady state currents at short response times. In addition, cyclic voltammetry experiments were performed using conventional potentiostats due to the amplification of current inherent in the array format. Electrochemiluminescence (ECL) at the ring electrode array was demonstrated through the oxidation of $Ru(bpy)_3^{2+}$ in tri-n-propylamide in a pH 7 phosphate buffer solution, where the light generated was collected and detected via the fiber bundle.

Figure 1:
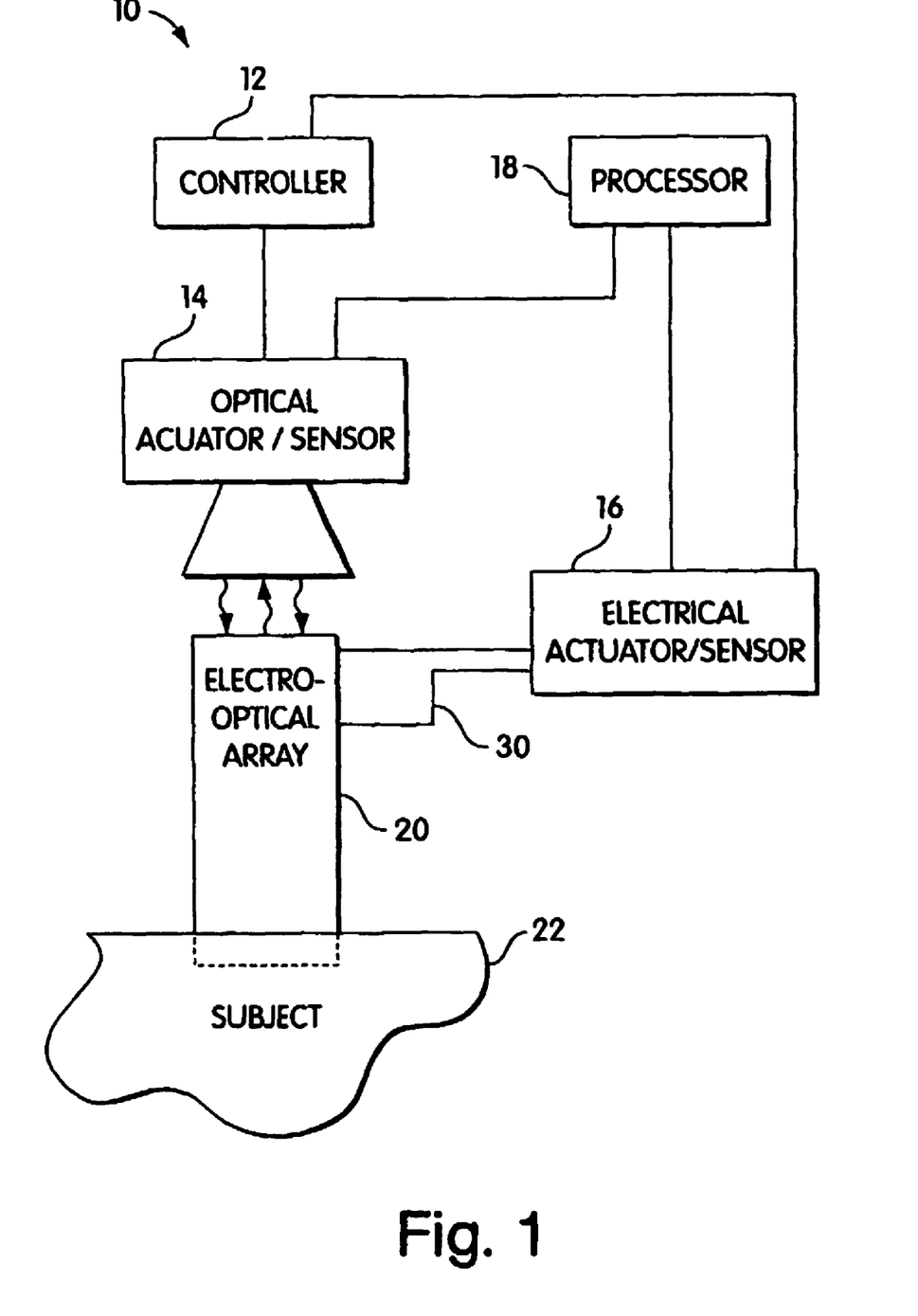
FIG. 1 is a simplified diagram of an electro-optical system for providing electrical and/or optical stimuli and measuring electrical and/or optical output.

Referring to FIG. 1, a system 10 includes a controller 12, an optical actuator/sensor (A/S) 14, an electrical actuator/sensor (A/S) 16, a processor 18, an electro-optical array 20, and a subject 22. The controller 12 is, e.g., a computer, and is configured to provide control signals to the optical A/S 14 and the electrical A/S 16. These control signals may be in response to information provided to the controller 12 from the A/Ss 14, 16. The processor 18 is configured to obtain information from the A/Ss 14, 16 and process this information into meaningful results for a user of the system 10. The optical A/S 14 includes a charge-coupled device (CCD) camera 15 (see FIG. 2) as the sensor and a light source as the actuator. The actuator portion of the electrical A/S 16 is a potentiostat.

The potentiostat is a PGSTAT 30 Autolab (made by Eco Chemie of Utrecht, Netherlands). The potentiostat is configured to apply DC voltages to the array 20, e.g., ramping from a lower voltage to a higher voltage and returning to the lower voltage. For example, the potentiostat can apply electricity of voltages starting at 0 V, increasing to 0.6 V, and returning to 0 V, at a rate of 0.02 V/s.

Figure 2:
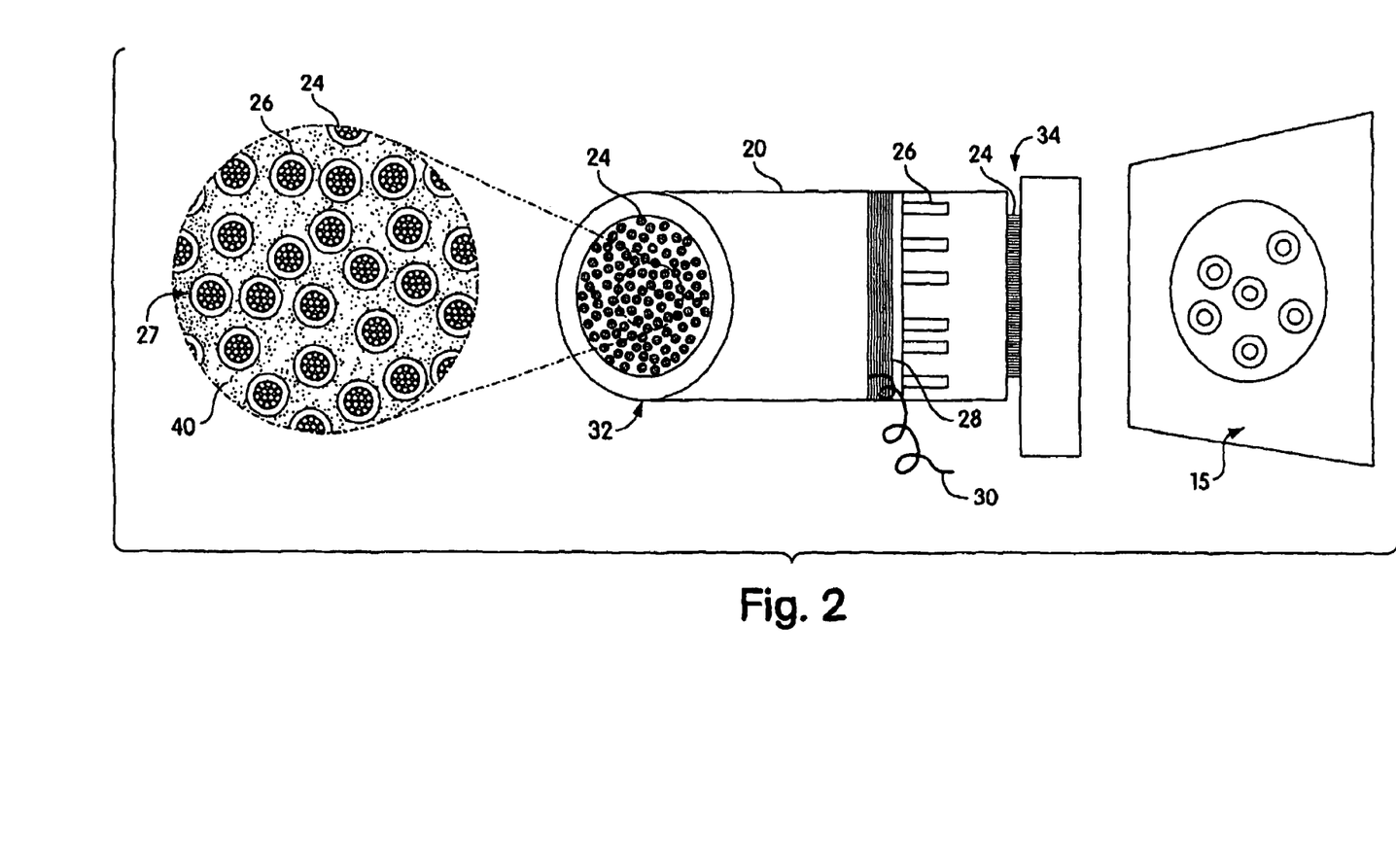
FIG. 2 is a schematic diagram of an electro-optical array shown in FIG. 1.

Referring also to FIG. 2, the array 20 is a bundle of fiber/electrode pairs 27 of optical fibers 24 with conductive coatings forming electrodes 26 around the fibers 24. The fibers 24 are raw glass made of fused silica glass from Edmund Industrial Optics of Barrington, N.J. Each fiber 24 has a 25 µm diameter and a length of about 10 cm. Approximately 600 fibers 24 are disposed in the array 20. The fibers 24 can transfer light from a distal end 32 to a proximal end 34, and vice versa. The distal end 32 and the proximal end 34 are both preferably relatively flat in order to properly focus light/electricity to/from the subject 22 at the distal end 32 and to/from the optical A/S 14 and/or the electrical A/S 16 at the proximal end 34. The fiber pairs 27 are not coherently related at the distal and proximal ends 32, 34. That is, it is unknown which distal end corresponds to which proximal end of a single fiber pair 27 (the distal and proximal ends of each fiber pair 27 do not appear in the same location of the distal and proximal ends 32, 34 of the array 20). The fiber pairs 27 are embedded in epoxy 40 that holds the pairs 27 together.

The electrodes 26 are gold and are coaxial with the fibers 24, extending along the cylindrical lengths of the fibers 24. Although gold has some advantages, e.g., good deposition properties, numerous other electrically-conductive material is acceptable including, but not limited to, silver, platinum, and electrically-conductive polymers (e.g., polythiophenes, polyanilines, and polypyrroles). Typical thickness of the gold plating is about 0.3 m; thus, the electrodes 24 have a typical outer radius of 12.8 µm (with an inner radius being approximately 12.5 µm, the diameter of the fibers 24). As shown in FIG. 2, the electrodes 26 extend partially along the lengths of the fibers 24 (with six of the electrode/fiber pairs indicated, for clarity). A contact layer is connected to the set of electrodes 26 where the deposited gold layer extends further than the other electrodes 26 (to allow only about 33% of the electrodes to be connected). Alternatively, only about 33% of the total fiber bundle can be coated with gold, the coated fibers mixed with the non-coated fibers, and the contact layer 28 connected to the coated fibers. A wire 30 couples the contact layer 28 to the electrical A/S 16.

The subject 22 can be a substance and/or an object such as a person. Preferably, the subject 22 is or contains a substance that reacts to either light or electricity and responds to this stimulus by emitting energy in the other form, i.e., responding to light be emitting electricity or responding to electricity by emitting light (electrochemiluminescence (ECL)). For example, the subject 22 can be a person with an injected antibody that reacts to electrical stimulation by luminescing. Additionally, the subject 22 can be a sample solution to be analyzed.

Assembly

Figure 3:
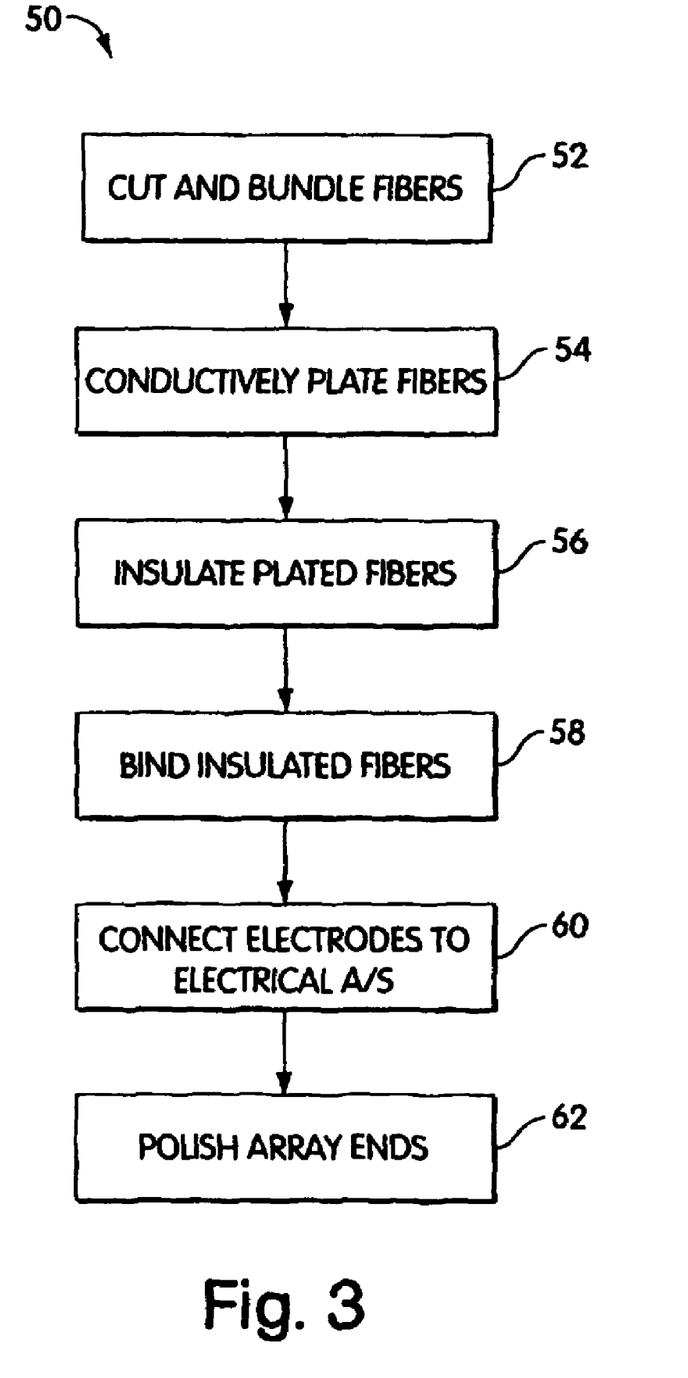
FIG. 3 is a block flow diagram of a process of assembling the array shown in FIG. 2.

Referring to FIG. 3, with further reference to FIG. 2, a process 50 of making the array 20 includes the stages shown. The process 50, however, is exemplary only and not limiting. The process 50 can be altered, e.g., by having stages added, removed, or rearranged. For the process 50, $SnCl_2$, tris(2,2'-bypyridyl)ruthenium (II) chloride hexahydrate, tri-n-propylamine, 11-mercapto-1-undecanol, trifluoroacetic acid, formaldehyde, $H_2SO_4$, $AgNO_3$, $Na_2SO_3$, $H_2O_2$, $NH_4OH$, methanol, ethanol, nitric acid from Sigma-Aldrich of Highland, Ill., and a commercial gold-plating solution ($Na_3Au(SO_3)_2$, Oromerse SO Part B, (5.67 g/100 ml) from Technic Inc. of Cranston, R.I., may be used.

At stage 52, approximately 600 of the fibers 24 are cut to lengths of about 10 cm and bundled at the proximal end 34. Bundling is accomplished using a 1 cm rubber tube acting as an O-ring.

At stage 54, the fibers 24 are plated with gold by having gold nanoparticles deposited around the surface of the individual optical glass fibers 24. The particles are deposited using an electroless deposition method similar to that described in Kobayashi et al., *Analytical Chemistry*, 1999, vol. 71, page 3665. The fibers 24 are immersed into 'piranha solution' (70% $H_2SO_4$, 30% $H_2O_2$), rinsed with water and methanol, and dried (Caution: 'piranha solution' reacts violently with organic materials). These cleaned fibers 24 are immersed for approximately 20 minutes into a solution of 0.026 M $SnCl_2$ and 0.07 M trifluoroacetic acid in 50% v/v methanol/water. This procedure deposits a $Sn^{2+}$ "sensitizer" onto the glass surface of the fibers 24. The fibers 24 are thoroughly rinsed with methanol and immersed into an aqueous solution of ammonical $AgNO_3$ (0.035 M) for 15 minutes. This leads to the deposition of silver nanoparticles on the fibers 24 while oxidizing the surface-bound $Sn^{2+}$ to $Sn^{4+}$. The silver-deposited fibers 24 were rinsed with methanol and water. These silver-coated fibers 24 are immersed, while stirring, in an aqueous solution of 0.079 M $Na_3Au(SO_3)_2$, 0.127 M $Na_2SO_3$ and 0.625 M formaldehyde for about 60 minutes in a water bath of 4° C. Formaldehyde is oxidized catalytically by the silver particles and gold is reduced concurrently to elemental gold and deposited on the fiber surface. The gold-coated fibers 24 are rinsed thoroughly with water and immersed, e.g., overnight, into 25% nitric acid solution to dissolve residual Ag and Sn particles exposed on the surface of the fiber 24. The gold-covered fiber is rinsed with methanol and water, and dried. The final products, the electrodes 26, are dark red to golden yellow, depending on the thickness of the gold coatings.

At stage 56, a self-assembled monolayer (SAM) is deposited on the surface of the gold-coated fibers 27 to insulate the pairs 27. The SAM is deposited by immersing the pairs 27 into ethanolic solutions containing 10 mM 11-mercapto-1-undecanol. This helps to prevent each fiber pair 27 from electrically contacting other fiber pairs 27.

At stage 58, the insulated fiber pairs 27 are bound to help further process and use the bundled fiber pairs 27. These insulated fiber pairs 27 are dipped into an epoxy polymer that is cured at 100° C. in an oven for several hours. For example, Araldite AM 136/Hy 994 insulating epoxy from Ciba Geigy of East Lansing, Mich. may be used. The coating helps enable polishing of the distal ends 32 of the fiber pairs 27. The coating also helps ensure total light reflection in the fibers 24. The fiber pairs 27 are bound such that their center-to-center spacing is about 30-100 µm to help ensure that diffusional overlap at longer electrode-stimulation times is reduced such that it can be considered to be negligible, and therefore not accounted for. For example, it has been suggested that for diffusion to be neglected, the ratio of the edge-to-edge inter-electrode distance d to the radius r of the electrode has to be $d/r \geq 20$. To meet this criteria in this case, an average spacing greater than or equal to $r*20 = (12/5 \ \mu m)*20 = 250 \ \mu m$ is needed.

At stage 60, approximately 20-30% of the electrodes 26 are electrically wired to the copper wire 30 through the contact layer 28, here a silver paste. For example, epo-tek H20E from Epoxy Technology of Billerica, Mass. may be used. The silver paste is applied only to the longer electrodes, and the wire 30 is electrically connected to the layer 28, e.g., by inserting the wire 30 into the paste 28 before curing of the paste 28. Connecting less than all of the electrodes 26 for coupling to the electrical A/S 16 helped to minimize diffusional overlap at longer stimulation times of the electrodes 26.

At stage 62, the ends 32, 34 of the array 20 are polished. The array 20 is polished with 30-15-3-0.3 µm lapping films made by General Fiber Optics of Fairfield, N.J. to expose the ring electrodes 26 around the optical fibers. The polishing also helps ensure a planar surface at the ends 32, 34 for proper focusing of light.

Operation

Figure 4:
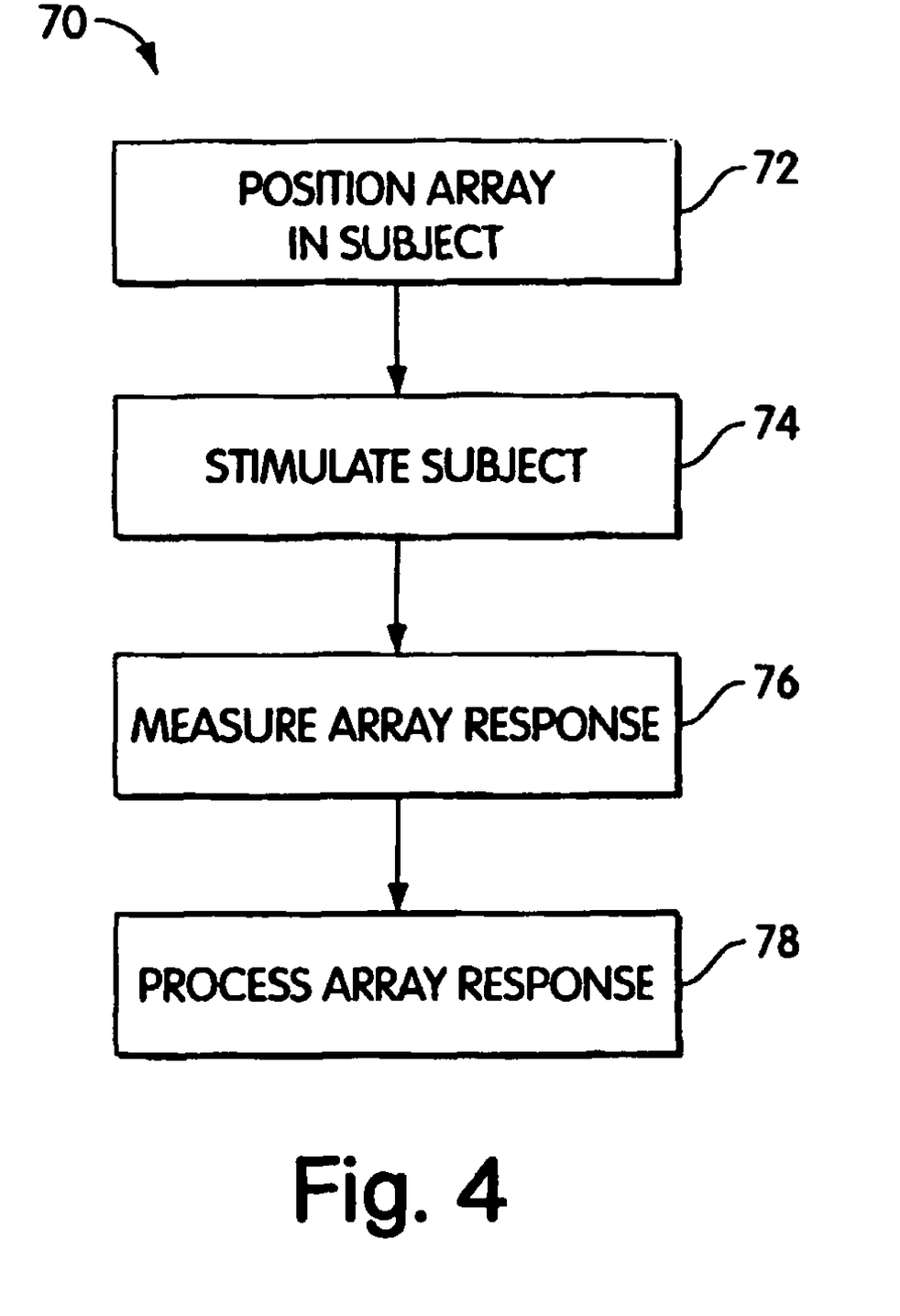
FIG. 4 is a block flow diagram of a process of using the system of FIG. 1.

In operation, referring to FIG. 4, with further reference to FIGS. 1-2, a process 70 for stimulating the subject 22 and measuring and processing the response using the system 10 includes the stages shown. The process 70, however, is exemplary only and not limiting. The process 70 can be altered, e.g., by having stages added, removed, or rearranged.

At stage 72, the array 20 is positioned for stimulating and measuring the subject 22. The distal end 32 of the array is inserted into the subject 22, e.g., a person. If desired, a chemical, such as an antibody, is injected into the subject 22 in the vicinity of the distal end 32 in a region to which the array 20 can apply electrical and/or optical stimuli to the chemical and from which the array can receive electrical and/or optical responses.

At stage 74, a stimulus is provided to the subject in the vicinity of the distal end 32 of the array 20. The controller 12 sends signals to cause the optical A/S 14 to provide light to the proximal end 34 of the array 20 and/or to cause the electrical A/S 16 to provide electricity to the electrodes 26. Both light and electricity can be applied to the subject 22 concurrently via the array 20. The stimuli are carried by the fibers 24 and/or the electrodes 26 and are radiated by the distal end 32 of the array 20 into the subject 22.

At stage 76, the array 20 measures the reaction by the subject 22. The subject 22 responds to the stimuli provided by the array 20 by emitting electricity and/or light. The emitted energy is received by the distal end 32 of the array 20 and transferred along the fiber pair 27 toward the proximal end 34 of the array 20. Optical and electrical energy can be sensed concurrently or one at a time. Optical and electrical energy sensed concurrently can be sensed independently such that the sensed energies can be distinguished. If the energy transferred along the fiber pair 27 includes electrical, then the contact layer 28 conveys the energy to the wire 30 to the electrical A/S 16. If the transferred energy includes light, then the light is conveyed from the proximal end 34 to the optical A/S 14, and in particular an optical sensor such as a CCD camera.

At stage 78, the measured energy from the subject 22 is processed. The optical A/S 14 and/or the electrical A/S 16 output indicia of the measured response to the processor 18. The processor 18 receives these indicia, processes the indicia in accordance with stored software, and outputs information, indicative of the subject's response, for a user.

Use

Arrays of sensors/actuators are used for various applications. Using multiple sensors/actuators with an array, multiple portions of a system (e.g., cell, analyte, material, or person) may be stimulated or measured simultaneously and independently by using disparate portions of the array.

An optoelectrochemical microarray is used for industrial detection purposes, as well as clinical diagnostic and therapeutic applications. For example, the array is useful to gather data from electrochemiluminescence-based assays in which chemical compounds emit light when electrochemically stimulated.

Compositions are addressed electrochemically and measured optically. Alternatively, compositions are addressed optically (or photochemically) and measured electrically. Fluorescent or light-emitting compounds such as ruthenium metal-based compounds, ruthenium tris-bipyridyl compound $(Ru(bpy)^{32+})$, are used as labels for sensing biological compounds in sensitive and precise assays. Other fluorescent or light-emitting compounds include oxo-Mo(IV) complexes [Mo(Tp(Me,Me))(O)Cl(L)] (L=py, phpy or monodentate bpy; abbreviated as Mo(py), Mo(phpy), and Mo(bpe), respectively), Nile Blue, daunomycin, 1,1'-bis(diorganophosphino) ferrocene-osmium(II) complexes, Rhenium(I) coordinated lumazine and pterin derivatives, porous silicon, conducting polymers (e.g polythiophenes, polyanilines, polypyrroles, poly(2,5-dioctyloxy-p-phenylene vinylene)). Numerous other labels are known in the art and are commercially available, e.g., from Molecular Probes, Inc. of Eugene, Oreg. Typically, the labels are excited when exposed to an electrical current, e.g., at the surface of an electrode in an array; upon excitation, the compound emits light and is regenerated. Labels may undergo several excitation/emission cycles, thereby amplifying the light signal and increasing sensitivity.

An amount of analyte in a sample is determined by measuring the emitted light and correlating the intensity of emitted light with the concentration of analyte. Examples of tags that are addressed photochemically and measured electrically include methylviologen and other viologens, porous silicon, and conducting polymers (e.g., polythiophenes, polyanilines, polypyrroles, poly(2,5-dioctyloxy-p-phenylene vinylene)).

The array is used to gather data from in vivo or in vitro immunoassays. A photon-emitting tag such as a fluorescent compound conjugated to an antibody or other specific ligand is used to detect a particular cell type or release of a particular compound, e.g., a cytokine or neurotransmitter, by a cell. For example, a fluorescent tracer is infused into brain tissue, and the microarray assembly is used to locally measure release of neurotransmitters by measuring light emission from the fluorescent tracer. The device yields qualitative as well as quantitative data regarding the analyte. For diagnostic purposes, a tumor-specific antibody tagged with a light-emitting compound such as ruthenium tris-bipyridyl compound $(Ru(bpy)^{32+})$ is injected or infused into a bodily tissue, and the antibody allowed to bind to its cognate ligand. After washing or clearing of unbound antibody, the microarray assembly is used to electrically stimulate the area to be diagnosed. Cells to which antibody is bound (i.e., tumor cells) emit light, which is detected by the array. Thus, diagnosis/detection of cells expressing a tumor antigen is accomplished on a cell-by-cell basis.

The array is also used to electrically excite a specific cell (e.g., identified optically using a cell-specific tag as described above) without exciting neighboring or adjacent cells, which have not been targeted for pulsing. Similarly, the array is used to preferentially destroy or inhibit the growth of specific cells (e.g., which have been identified optically) without affecting neighboring or adjacent cells which were not targetted for growth inhibition or destruction. Following detection of individual cancer cells, a pulse of electricity is specifically administered to the tumor cells, while sparing non-tumor cells in the tissue. The specificity of the therapeutic methods exceeds most traditional therapies. Prior or simultaneous identification of target cells and destruction/excitation of specific target cells (without affecting "non-target" cells) reduces unwanted side effects (e.g., destruction of healthy "non-target" cells) often associated with traditional cancer therapies.

Experiments

Experiments were performed using the system 10, with array 20 being as described above. The array 20 included approximately 600 fibers of 10 cm length and 25 m diameter. The fibers 24 were gold-plated to form the electrodes 26. Approximately 20-30% of the electrodes 26 were connected through the contact layer 28 to the wire 30. The fibers 24 were embedded in an insulating polymer and the distal end 32 of the array 20 was polished to expose gold-ring microelectrodes. The array 20 of micro-ring electrodes was characterized using FE-SEM. Cyclic voltammetry and chronoamperometry were performed to characterize the electrochemical behavior of the micro-ring array. The array 20 was examined for its applicability for spectro-electrochemical problems. Subjects 22 of an aqueous $Fe(CN)_6^{4+}$ solution and electrogenerated chemiluminescence with tris(2,2'-bypyridine)ruthenium (II) $(Ru(bpy)_3^{2+})$ in the presence of tri-n-propylamine (TPrA) were used.

The instrumental set up for imaging and fluorescence measurements is described in detail in Bronk et al., *Analytical Chemistry*, 1995, vol. 67, p. 2750. The array 20 was fixed in a cell (V=1 ml) containing the counter electrode of the potentiostat (e.g., a platinum wire) and the reference electrode of the potentiostat (e.g., a silver wire) and mounted on the stage that supports the imaging system 10 and the subject 22. No excitation wavelength was used as $Ru(bpy)_3^{2+}$ was excited electrochemically. The ECL returning through the optoelectrochemical array 20 was transmitted through a dichroic mirror and detected by a CCD camera (model PXL-37 made by Photometric of Tucson, Ariz.). The emission wavelength for $Ru(bpy)_3^{2+}$ is 670 nm. Images were collected every 500 ms for 400 ms either by scanning the potential from 0.8 to 1.3 V/Ag/AgCl (scan rate=0.02 V s$^{-1}$) or by applying a potential of 1.2 V/Ag/AgCl to the array 20. SEM images were obtained with a field emission scanning electron microscope (FE-SEM; model 982 made by LEO Electron Microscopy, Inc. of Thornwood, N.Y.) located at Harvard University.

The potentiostat used was a PGSTAT 30 Autolab (made by Eco Chemie of Utrecht, Netherlands). Experiments were performed using either a SCE or Ag/AgCl reference electrode. The counter electrode was a platinum wire. Solutions were purged with nitrogen. In all experiments, a low-current amplifier and a Faraday cage were used (model C2 made by Bioanalytical Systems, of West Lafayette, Ind.).

SEM

Figure 5:
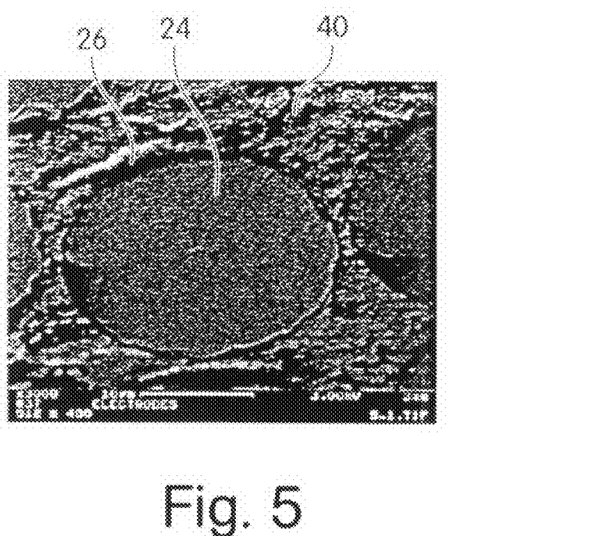
FIG. 5 is an FE-SEM image of an optical fiber embedded in epoxy of the array shown in FIG. 1.
Figure 6:
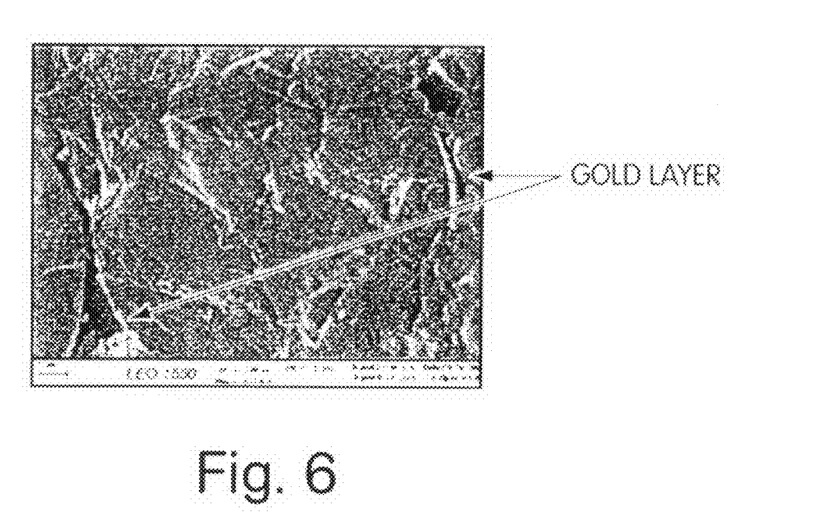
FIG. 6 is an FE-SEM image of an outer gold layer of a fiber/electrode pair shown in FIG. 2.

FIG. 5 shows an FE-SEM of some fiber electrodes 26 of the random assembly embedded in the epoxy structure 40. The fibers 24 are insulated from their neighbors by the epoxy 40. The center-to-center distance of the fibers 24 is between about 30 and 100 m. This distance would be too close to avoid diffusional overlap at longer electrode-stimulation times. This overlap was overcome by connecting only about 20-30% of the fiber/electrodes 27. FE-SEM was further used to visualize the gold layer around the ring. As the optical fibers 24 are not conducting, charging effects are seen in FIG. 6. The gold ring is seen as the bright region around the optical fiber 24 and its thickness is estimated as being roughly 300 nm.

Cyclic Voltammogram

When designing random assemblies of electrodes, care should be taken to avoid diffusional interference between adjacent electroactive areas. A careful design is preferred if an assembly of micro-ring electrodes is to show steady state currents that are several times larger than a single microelectrode. Such a device, based on the electroless deposition of gold around optical fibers, was formed by connecting only 20-30% of the 600 gold-covered fibers in the bundle. This procedure helped to maximize the preference for the individual rings to be spaced by ca 250 m, so that interferences due to diffusional overlap would be reduced, and possibly minimized.

Figure 7:
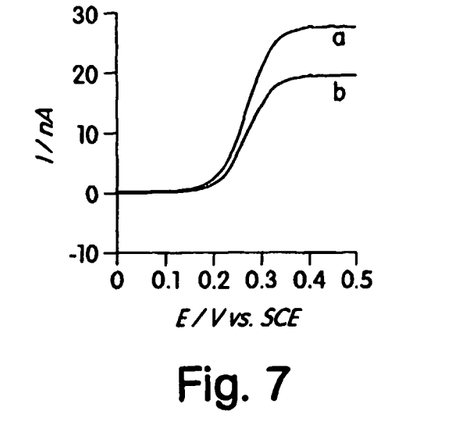
FIGS. 7-9 are cyclic voltammograms of a disk electrode (a) with a 25 m diameter, and of a fiber/gold ring electrode (b) (FIG. 7), a microarray with a self-assembled thiol monolayer (FIG. 8), and a microarray without a self-assembled thiol monolayer (FIG. 9), using a solution of 10 mM $Fe(CN)_6^{4-}$/0.1 M KCl and a scan rate of 0.01 V/s.

Steady-state current-potential curves were recorded, enabling determining the number of active electrodes in the array and obtaining some indication about the spacing between electrodes. FIG. 7 shows cyclic voltammograms of a disk electrode (r=12.5 m) and a gold-particle coated single fiber (r=12.5 m+0.3 m gold) polished on its end to expose a micro-ring electrode. The micro-ring fiber/electrode shows a sigmoidal waveform at slow scan rates. An initial estimate of the size of the electrode ring can be made by measuring the steady state current $i_{disk}$ recorded with a disk microelectrode of the same outer radius b through its steady state current and applying $$i_{disk}=4nFD_{Fe(II)}c_{Fe(II)}b. \tag{1}$$

In equation (1), n is the number of electrons, F is the Faraday constant, D is the diffusion coefficient ($D_{Fe(II)}$=6.0×10$^{-6}$ cm s$^{-1}$), c the concentration of the electroactive species (c=10 mM), and b the outer ring radius (b=12.8 m) respectively.

According to Wallingford et al., *Analytical Chemistry*, 1988, vol. 60, p. 1972, the limiting steady-state current of a ring can be predicted from the current of a disk electrode of equal radius. Taking account of the 300 nm gold layer around the fiber (b=$r_{fiber}$+300 nm gold), the outer radius of the ring/fiber is b=12.8 m and the current should reach a plateau at $2.96 \times 10^{-8}$ A for a disk electrode. As seen in FIG. 7, however, the current recorded on the micro-ring is slightly lower compared to a disk electrode with the same outer radius. The numerical difference in steady state current for the ring compared to the disk electrode is about 67%. It has been shown that for a ratio of inner radius/outer radius a/b=0.97, the ring current is only 68% of the disk, a value that compares nicely with ring electrode implemented here, with a=12.5 m and b=12.8 m. Therefore a ring-disk-shaped electrode with inner radius a and outer radius b should result in 33% smaller currents than a comparable disk electrode with the same radius b.

The current of a single gold-coated fiber ring was used as a reference for estimating the number of active rings in the high-density array. Ideally, an array with N active microelectrodes should yield a current amplification relative to a single electrode by a factor of N.

$$i_{array} = N \cdot i_{micro} \quad (2)$$

In practice, these expectations are fulfilled only if certain very strict requirements concerning the array design are met. If the electrodes 26 are too closely packed, their diffusion layers will overlap and the current response approaches that of a macroelectrode.

Figure 8:
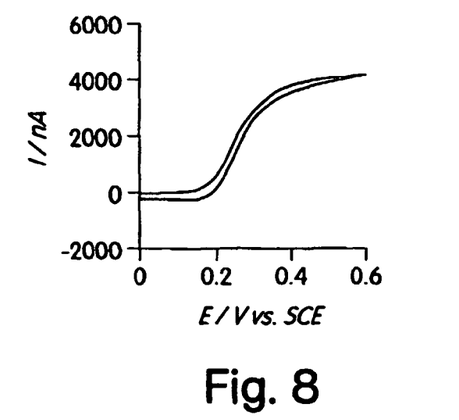

FIG. 8 shows the voltammogram of the microelectrode array 20 in a 10 mM aqueous solution of ferrocyanide. The steady state current responses were preserved in this array format and give a useful qualitative indication that the spacing between the active ring sites is sufficient such that the diffusion fields do not overlap, at least substantially so. Some overlap of diffusion layers may still take place as the arrangement of the electrodes and its connection was random and proved to be difficult to control. Depending on the particular array 20, some areas of the device have electrodes 26 that are clustered, while in other parts the distance for non-diffusional overlap is observed entirely. Furthermore, if two electrodes 26 touch each other microelectrode behavior would be observed with steady state currents, as the final diameter of these ring fiber electrodes would be 50 m. As there are approximately 200 ring electrodes 26 in the array 20, the error in the steady state current should be minimal. The limiting current was used as an indication and a first approximation of the number of active sites on the array 20. The number of active sites N is estimated by dividing the limiting current of the array 20 by the limiting current for a single fiber electrode 26 (FIG. 7) performed under the same conditions. Using this assumption, it was estimated that about 200 micro-ring electrodes 26 were active.

Figure 9:
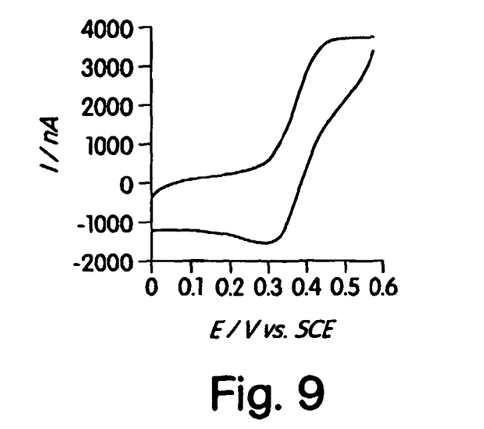

As discussed above, the cyclic voltammogram (CV) shows the characteristic shape for spherical and nonplanar diffusion at microelectrodes and suggests that the majority of the electrodes 24 are separated and that the diffusion layers do not overlap significantly. If interelectrode spacing was not large enough, a characteristic macroelectode shaped CV peak would have been observed. The incomplete reversibility of the steady state current might be an indication that some electrode profiles may overlap. The SAM layer was important in obtaining these steady state results. FIG. 9 shows the CV of an assembly where the gold-deposited array was only sealed into epoxy. As seen in the figure, the current height of the device is the same, but instead of an expected steady state current, a peak shaped CV was observed. This result can be explained by the fact that some of the electrodes 26 were in close contact leading to a characteristic macroelectrode response.

Chronoamperometry

To verify the assumption that large spacing between the individual rings exists, chronomamperometric measurements were undertaken. The current vs. time dependency of a micro-ring electrode can be considered as a limiting case of a band at short times and a disk microelectrode at longer electrode-stimulation times. The current on a micro-disk and a micro-ring electrode can approach a steady state value while the current on a band microelectrode decays with the reciprocal logarithm of time. Similar to a band electrode, the ring microelectrode has a higher perimeter-to-area ratio than the disk microelectrode. Many contributions have been devoted to developing a theory of the diffusion controlled steady-state current lim i(t) of bands and disks. The steady state behavior for a ring electrode has been described in Szabo, J. Phys. Chem., 1987, vol. 91, p. 3108 and Fleischmann et al., J. Electroanal. Chem., 1987, vol. 222, p. 107, where lim i(t) was calculated assuming uniform accessibility to the surface of the ring electrode of arbitrary thickness. According to Szabo, the limiting current at time t at a micro-ring is given by $$\lim i(t) = nFDcl_0[1+l_0/(4^2Dt)^{1/2}]/l_0 = [^2(a+b)/\ln[32a/(b-a)+\exp(^2/4)] \quad (3)$$

where a is the inner ring radius, and b is the outer ring radius, respectively. This treatment assumes that the insulating sheet is infinitely thick and a uniform flux to the surface of the electrode 26 is maintained.

Figure 10:
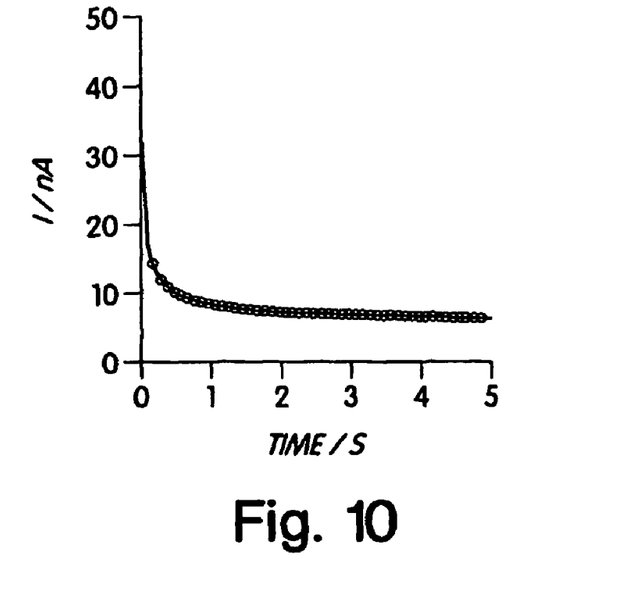
FIGS. 10-11 are comparisons of the chronoamperometric current (dotted line) of a single ring/fiber electrode (FIG. 10) and a microelectrode array with the limiting current predicted by Szabo (FIG. 11) using a solution of 10 mM $Fe(CN)_6^{4-}$/0.1 M KCl.
Figure 11:
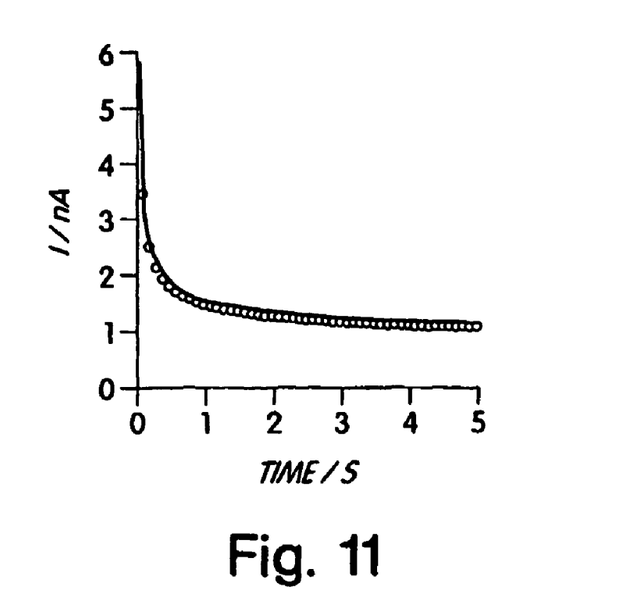

Chronoamperometric curves of one of the optical fibers coated with gold nanoparticles was recorded in 10 mM aqueous ferrocyanide solutions for times up to 5 s (FIG. 10). The experimental data shown in FIG. 10 (points) are in good agreement with the theoretically calculated ones (line) using equation (3) with the respective variables being: $D_{Fe(II)}=6.0 \times 10^{-6}$ cm s$^{-1}$, c=10 mM, a=12.5 m and b=12.8 m. In the case of a micro-ring array, the chronomamperometric response depends on the time frame of the experiment. At short times, where each individual ring is separated and no interference from overlapping diffusion is expected if the interelectrode distance is sufficiently large, the current decay should be 1/sqr(t), as described by Szabo and show Cotrellian behavior. From the chronoamperometric signal of the array in FIG. 11, this value seems to be indeed the case if it is assumed that there are 200 individual active electrodes and the limiting current is multiplied by this factor. At longer times a more complex behavior is expected, changing from Cotrellian to cylindrical diffusion behavior (1/lnt) and finally to planar diffusion of the whole array (1/sqr(t),), resembling a macroelectrode.

If the thickness of the micro-ring is assumed to be 300 nm, the typical time expected to reach steady state current is in the order of $l^2/D^{26}$, where l is the characteristic dimension of the electrode 26. In the case of a ring, l is taken as the inner radius a of the ring and the time calculated to reach steady state behavior is 0.26 s, which is feasible taking into account that steady state currents develop rapidly at microelectrodes. Taking equation (4) as an approximation for the dimension of the diffusion layer developed on the ring, the thickness of will be 12 m. This value corresponds to the inner radius a of the ring/fiber electrode.

$$= sqr(Dt) \quad (4)$$

Figure 12:
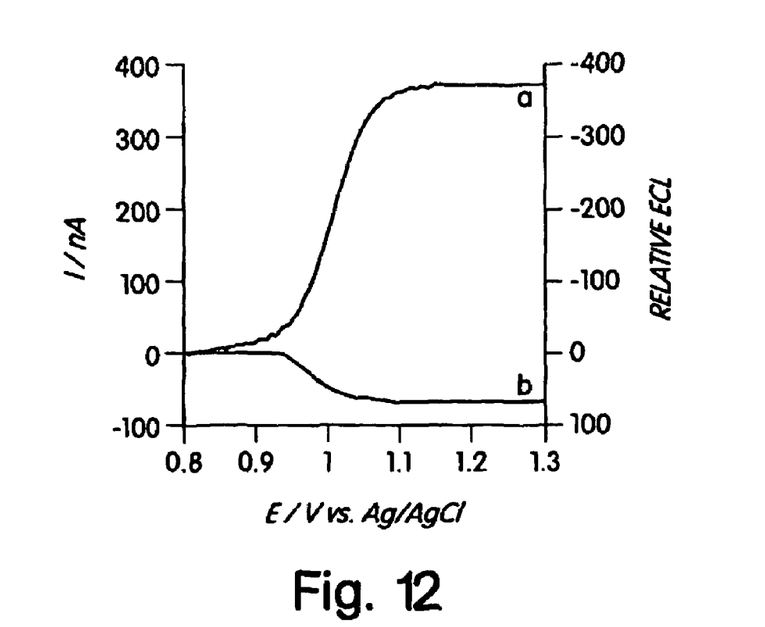
FIG. 12 is a diagram of development of electrochemiluminescence (ECL) intensity on an optoelectrochemical microarray, showing a voltammogram (a) and a corresponding ECL curve (b), with a scan rate of 2 mV/s and a solution of 1 mM $Ru(bpy)_3^{2+}$/0.1 M TPrA/0.15 M phosphate buffer (pH 7).

At 5 s, would have grown to around 60 m so that if the spacing between the electrodes is larger than 60 m, no diffusional interferences and therefore no macroelectrode behavior will be observed, as shown in FIG. 12.

Electrogenerated Chemiluminescence

Electrochemical oxidation of Ru(bpy)$_3^{3+}$ results in chemiluminescence in the presence of TPrA. Novel spectroelectrochemical sensors embodying two modes of instrumental selectivity, electrochemical and spectroscopic have been described by Gao et al., *Electroanalysis*, 2001, vol. 13, p. 613. A critical review of the analytical applications of Ru(bpy)$_3^{3+}$ as a chemiluminescent reagent has recently been published by Gerardi et al., *Anaytical Chim. Acta*, 1999, vol. 378, p. 1. The electrochemiluminescence (ECL) of an electrolyte solution results from the electron transfer reaction of ion radicals produced from an organic reactant that generates an excited state product and luminescence when it relaxes to its ground state. The ECL intensity is a quantitative characteristic of the rate of such an electron transfer reaction.

The aqueous system of Ru(bpy)$_3^{2+}$/TPrA was used to demonstrate that the micro-ring optical fiber array 20 can be used for the detection of light. The ECL mechanism of this system has been intensively investigated. At high concentrations of Ru(bpy)$_3^{2+}$ (>0.1 mM) the catalytic oxidation of TPrA by electrogenerated Ru(bpy)$_3^{3+}$ is the dominant process of ECL as described by the following equations:

$$\text{Ru}(bpy)_3^{2+} \rightarrow \text{Ru}(bpy)_3^{3+} + eE^0 = 1.26 \; V/SCE \quad (5)$$

$$\text{Ru}(bpy)_3^{3+} + TPrA \rightarrow \text{Ru}(bpy)_3^{2+} + TPrA^+ \quad (6)$$

$$TPrA^+ \rightarrow TPrA + H^+ \quad (7)$$

$$\text{Ru}(bpy)_3^{3+} + TPrA \rightarrow \text{Ru}(bpy)_3^{2+\ast} + \text{products} \quad (8)$$

$$\text{Ru}(bpy)_3^{2+\ast} \rightarrow \text{Ru}(bpy)_3^{2+} + h\nu \quad (9)$$

To perform ECL, the assembly 20 was placed into a voltammetric cell, comprising a 1 ml volume. A platinum plate counter electrode was placed parallel to the device. This positioning ensured that no reflected light from the platinum surface would be collected by the optical fibers. ECL was performed by stepping the potential from 0.0 V/Ag/AgCl, where no electrochemical reaction takes place, to 1.20 V/Ag/AgCl where oxidation of Ru(bpy)$_3^{2+}$ and the catalytic oxidation of TPrA occurs (FIG. 12). The ECL intensity increased rapidly at a potential more positive than 1.0 V reaching a constant level from 1.10-1.30 V/Ag/AgCl. Light was collected at 550-650 nm, the emission region of the Ru(bpy)$_3^{3+}$. When the potential was held constant at 1.20 V/Ag/AgCl the signal was stable for more than a minute before the fluorescence signal decayed. The rise in ECL emission reaches a steady state, but at times longer than the steady state of the diffusion layer, which was estimated as being 0.23 s (see chronoamperometry). ECL emission increases via an initial fast rise occurring at time constants on the order of 0.23, followed by a comparatively slow increase to the steady state limit. In this manner, the electrochemical properties of the ring and its ability to collect light with the same device were demonstrated.

Figure 13:
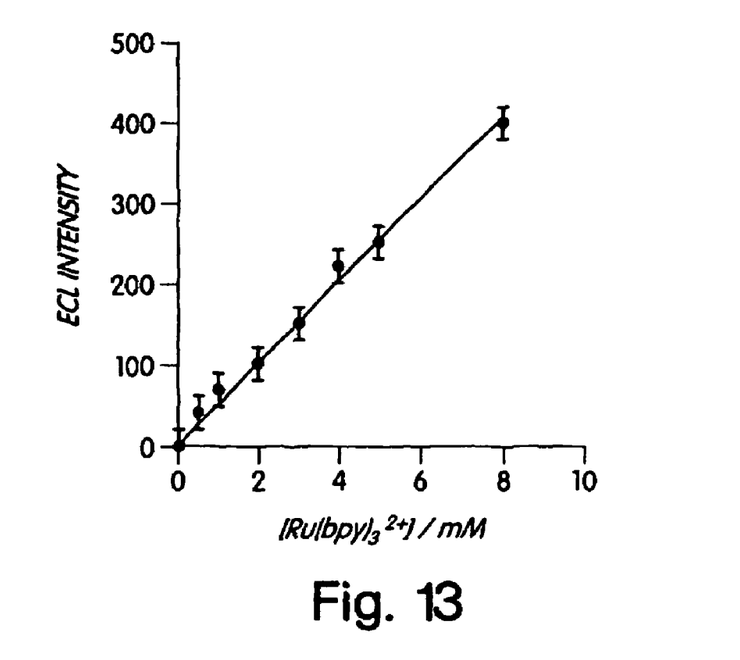
FIG. 13 is a diagram of a calibration curve for ECL using the microarray shown in FIG. 2, with $E_{app}$=1.2 V/Ag/AgCl using a solution of x mM $Ru(bpy)_3^{2+}$/0.1 M TPrA/0.15 M phosphate buffer (pH 7), where each point shown is an average of 5 trials.

The analytical utility of the chemiluminescence of Ru(bpy)$_3^{2+}$ depends on the emission of light, which is indicative of the concentration of the analyte in solution. The microarray was therefore exposed to different Ru(bpy)$_3^{2+}$ concentrations. FIG. 13 shows a calibration curve for the ruthenium system using the microarray. To obtain reproducible signals, after each trial, the electrode was cleaned by pulsing it several times to remove any adsorbed or deposited materials.

CONCLUSION

The array tested demonstrated that electrochemically-generated luminescent products can be detected with a fiber assembly. This device can be used as an optoelectronic sensor, especially for the electrolytic generation and transmission of ECL. While all the fibers 24 were optically addressable, not every fiber was electrochemically addressable. The resolution of the device was in the tens of micrometers range, determined by the diameter of the optical fibers 24 and by the spacing between each electrically-connected fiber. For the purpose of having well-behaved microelectrode characteristics, this spacing was designed to be larger than 60 m. An ordered optoelectrochemical device may overcome this limitation and should allow chemical and electrochemical sensing as well as imaging of surfaces with good spatial resolution Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Additionally, while the array 20 was described as being non-coherent and with electrode rings 26 disposed about optical fibers 24, an array can be coherent and/or have electrodes disposed within one or more optical fibers. For example, referring to FIG. 14, an array 100 includes electrodes 102, optical fiber rings 104, and epoxy 106 that holds the electrodes 102 and rings 104 in place. The electrodes 102 are capillaries filled with gold, or other suitable conductor. The rings 104 comprise material that helps guide light between ends of the array 100. The electrodes 102 are connected by a contact layer 108, to a wire 110, for connection to an electrical A/S (see FIG. 1). A CCD camera 112 is disposed near a proximal end of the array 100 for sensing light transferred through the array 100. The electrode/ring pairs 114 are coherent in the array 100, with the spatial relationship of the apertures of the pairs 114 at the distal end 116 relative to the proximal end 118 being known. Preferably, the pairs 114 are arranged the same at each end 116, 118 to help reduce processing of sensed energy at the proximal end 118. The coherency helps the array 100 be used for imaging, e.g., optical imaging of subjects disposed in the vicinity of the distal end 116. To help avoid diffusional overlap, the center-to-center spacing d of the electrodes 102 should obey the d/r≧20 guideline (d being the center-to-center spacing for solid electrodes 102 versus the edge-to-edge spacing for ring electrodes 26).

Figure 14:
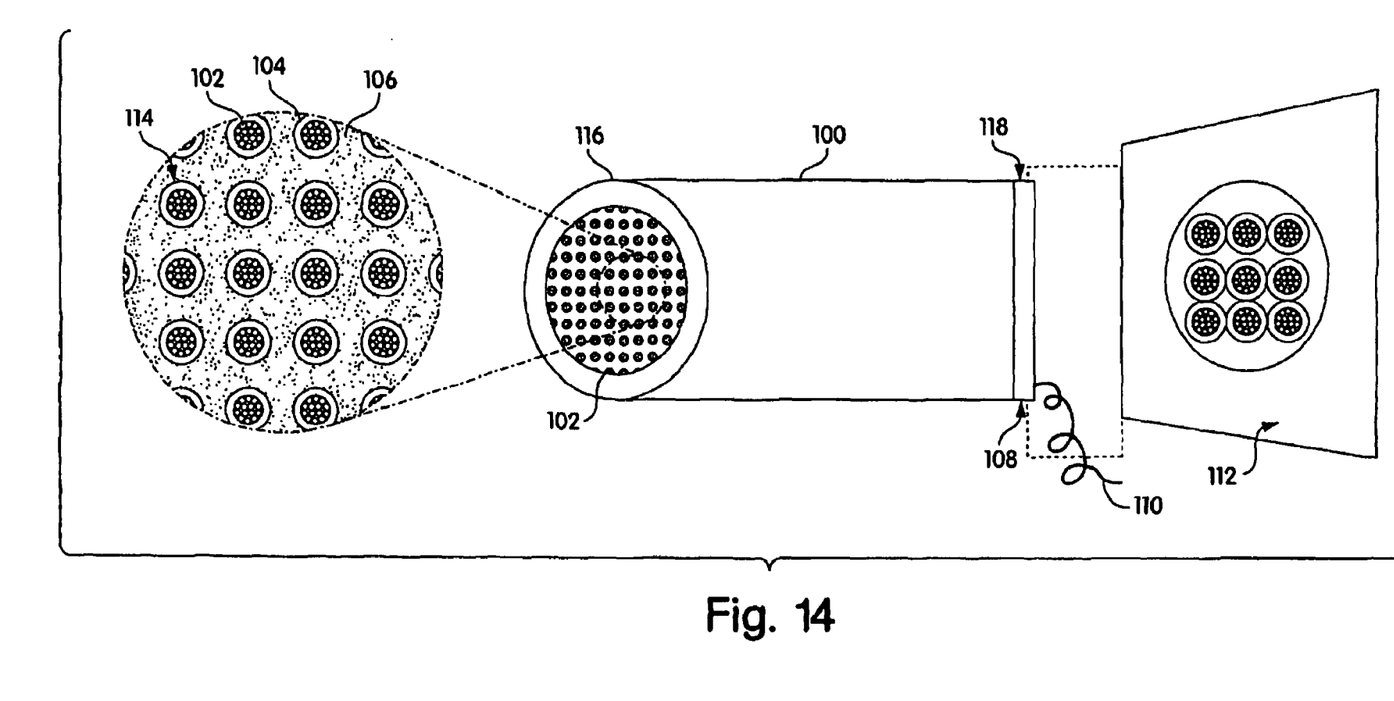
FIG. 14 is a schematic diagram of alternative electro-optical array to that shown in FIG. 2.

An array of electrodes can be used with a single optical transmission medium that also holds the electrodes in place. For example, the array 100 can be made using an optically-conductive, low-index-of-reflection (e.g., 1.56) substrate, in place of the epoxy 106, through which passages are formed. The passages can be clad with a high-index-of-reflection (e.g., 1.66) material, in place of rings 104. The clad passages can be filled with electrically-conductive material, such as gold, to form electrodes. The electrodes conduct electricity as desired, and the substrate acts essentially as a single optical fiber in which the electrodes disposed. The substrate can thus transfer light in the vicinity of the distal end of the array to the proximal end, with light being produced in different portions of the distal-end vicinity combining in the substrate.

Also, different amounts of optical fibers and electrodes, and different amounts of active electrodes than as discussed above are acceptable. For example, an array can have more or fewer, e.g., 100, optical fibers than the 600 fibers discussed above. Further, the amount of active electrodes can be different, e.g., approximately 50% of the total number of electrodes. Other percentages or relative amounts of active versus total electrodes are possible, with the desire being that the inter-electrode spacing be such that diffusional overlap is substantially negligible.

What is claimed is:

1. An electro-optical system comprising:
   an array comprising:
      a plurality of optical fibers configured to transmit light, the optical fibers being mechanically coupled at distal ends in a distal arrangement and mechanically coupled at proximal ends in a proximal arrangement; and
      a plurality of electrodes substantially coaxially disposed with at least portions of corresponding optical fibers, the electrodes being electrically conductive, with the electrodes and optical fibers being disposed in pairs, thereby being pair components, with one of the pair components of each pair being disposed about a radial periphery of the other pair component; and
      an insulator disposed between the plurality of electrodes and configured to inhibit transfer of electrical energy between the plurality of electrodes.

2. The system of claim 1 further comprising:
   an electrical apparatus coupled to at least some of the plurality of electrodes and configured to at least one of transmit electrical energy to, and receive electrical energy from, the at least some of the plurality of electrodes; and
   an optical apparatus configured and disposed to receive light from the proximal ends of the optical fibers.

3. The system of claim 2 wherein the electrical device is coupled to less than all the plurality of electrodes.

4. The system of claim 3 wherein the electrical device is coupled to a percentage of the electrodes such that diffusional overlap at distal ends of the electrodes will be substantially negligible.

5. The system of claim 4 wherein the electrical device is coupled to approximately 20-30% of the electrodes.

6. The system of claim 1 wherein the electrode of each pair is disposed about the radial periphery of the fiber of each pair.

7. The system of claim 6 wherein an edge-to-edge spacing between any two electrodes coupled to the electrical apparatus is greater than about 10 times a typical diameter of one the plurality of electrodes.

8. The system of claim 1 wherein the optical fiber of each pair is disposed about the radial periphery of the electrode of each pair.

9. The system of claim 8 wherein a center-to-center spacing between any two electrodes disposed coaxially with the at least some of the plurality of optical fibers is greater than about 10 times a typical diameter of one of the plurality of electrodes.

10. The system of claim 1 wherein the distal ends of the optical fibers correlate to the proximal ends of the optical fibers in a known manner.

11. The system of claim 1 wherein the distal arrangement and the proximal arrangement are substantially similar.

12. The system of claim 1 wherein the electrical apparatus is configured to at least one of transfer electrical energy to, and receive electrical energy from, the at least some of the plurality of electrodes as a group.

13. The system of claim 1 wherein the electrical apparatus is configured to at least one of transfer electrical energy to, and receive electrical energy from, the at least some of the plurality of electrodes individually.

14. The system of claim 1 wherein the electrodes comprise electrically-conductive material coating an outer surface of the optical fibers.

15. A method of stimulating and sensing an object, the method comprising:
   providing energy in a first form to the object through at least one of a plurality of first energy transmitters disposed in a first array at least at distal ends of the first energy transmitters, the first form of energy being one of electrical and optical; and
   sensing energy in a second form, produced by the object, through at least one of a plurality of second energy transmitters disposed in a second array at least at distal ends of the second energy transmitters, the first and second energy transmitters being mechanically coupled together and coaxially disposed at least at their distal ends, the second form of energy being one of electrical and optical, the second form of energy being different than the first form of energy.

16. The method of claim 15 wherein the first form of energy is electrical and the first energy transmitters are microelectrodes, and wherein the providing energy includes providing energy to all of the plurality of first energy transmitters.

17. The method of claim 15 wherein the first form of energy is electrical and the first energy transmitters are microelectrodes, and wherein the providing energy includes selectively providing energy to a portion of the plurality of first energy transmitters.

18. The method of claim 17 wherein the providing energy includes providing energy to the portion of the plurality of first energy transmitters such that diffusional overlap of the energy at distal ends of the portion of the plurality of first energy transmitters is substantially negligible.

19. The method of claim 15 wherein the first form of energy is electrical and the first energy transmitters are microelectrodes, and wherein the providing energy includes providing different amounts of energy to different ones of the plurality of first energy transmitters.

20. The method of claim 15 wherein either the first or the second energy transmitters are electrodes, the method further comprising providing electrical energy through the electrodes to kill living tissue in the object in a vicinity of distal ends of the electrodes.

21. The method of claim 15 further comprising processing the second energy to determine an image of at least a portion of the object.

22. The method of claim 15 further comprising providing energy in the second form to the object through at least one of the second energy transmitters.

23. The method of claim 22 wherein the providing energy in the first form and the providing energy in the second form occurs concurrently.

24. The method of claim 23 further comprising sensing energy in the first form concurrently with the sensing energy in the second form.

25. The method of claim 15 wherein the second energy transmitters are optical fibers, and the sensing includes sensing optical energy transmitted by at least two of the optical fibers.

26. The method of claim 15 wherein the first energy transmitters are optical fibers and the providing includes transmitting optical energy through less than all of the optical fibers.

27. An electro-optical actuator/sensor system comprising:

optical means for delivering light to an optical-fiber array;

electrical means for delivering electricity through an electrical array of microelectrodes, the electrical means comprising electrically-conductive cladding of the optical fibers in the optical-fiber array;

an electrical apparatus coupled to the electrical means and configured to transfer electrical energy between the electrical apparatus and selected ones of the microelectrodes; and an optical apparatus configured and disposed to transfer light between the apparatus and the optical-fiber array.

28. The system of claim 27 wherein distal and proximal ends of the optical fibers and electrodes are coherently related.

29. The system of claim 27 wherein the electrical apparatus is coupled to transfer electrical energy to about 20-30% of the electrodes.

30. The system of claim 27 wherein distal ends of the electrodes are disposed proximate to distal ends of the optical fibers and are separated from each other such that diffusional overlap associated with the electrodes is substantially negligible.

31. An electro-optical array comprising:

an optical substrate configured to transmit light, the substrate defining a plurality of openings extending through a thickness of the substrate;

a plurality of electrodes disposed within the openings through the substrate; and at least one electrical conductor coupled to a portion of the plurality of electrodes, the at least one electrical conductor being configured to couple to an apparatus for supplying current to, and receiving current from, the at least one electrical conductor.

32. The array of claim 31 further comprising a plurality of optical rings disposed within the plurality of openings between the substrate and the electrodes, the optical rings having a higher index of reflection than the substrate.

33. The array of claim 31 wherein the openings defined by the substrate extend substantially straight through the substrate.

34. The array of claim 31 wherein distal ends of the electrodes are disposed relative to each other in a distal arrangement, and proximal ends of the electrodes are disposed relative to each other in a proximal arrangement, and the distal and proximal arrangements are substantially similar.

35. The array of claim 31 wherein the portion of the electrodes is such that diffusional overlap from distal ends of the electrodes is substantially negligible.

36. The array of claim 35 wherein the portion of the electrodes comprises approximately 50% of the electrodes.

37. The array of claim 35 wherein the portion of the electrodes comprises approximately 20-30% of the electrodes.

38. A method of specifically stimulating a target cell in a population of non-target cells, comprising:

providing energy, using a portion of an array of energy transmitters, to cells that include said target cell and said non-target cells;

detecting an optical signal, using another portion of said array of energy transmitters, to identify said target cell; and delivering an electrical current, using yet another portion of said array of energy transmitters, to said cell;

wherein said electrical current is substantially not delivered to a non-target cell and wherein said target cell is stimulated to transduce an intracellular or extracellular signal.

39. A method of specifically destroying a target cell in a population of non-target cells, comprising:

providing energy, using a portion of an array of energy transmitters, to cells that include said target cell and said non-target cells;

detecting an optical signal, using another portion of said array of energy transmitters, to identify said target cell; and delivering an electrical current, using yet another portion of said array of energy transmitters, to said cell;

wherein said electrical current is substantially not delivered to a non-target cell and wherein said target cell is destroyed.

* * * * *